(12) United States Patent
Doisaki et al.

(10) Patent No.: US 9,029,584 B2
(45) Date of Patent: May 12, 2015

(54) METHOD FOR PRODUCING OIL CONTAINING HIGHLY UNSATURATED FATTY ACID USING LIPASE

(75) Inventors: Nobushige Doisaki, Hachioji (JP); Hideo Ikemoto, Hachioji (JP); Kazuhiko Hata, Kamisu (JP); Shinji Tokiwa, Kamisu (JP); Kazunori Matsushima, Tokyo (JP)

(73) Assignee: Nippon Suisan Kaisha, Ltd. (JP)

( * ) Notice: Subject to any disclaimer, the term of this patent is extended or adjusted under 35 U.S.C. 154(b) by 7 days.

(21) Appl. No.: 14/002,806

(22) PCT Filed: Mar. 2, 2012

(86) PCT No.: PCT/JP2012/055334
§ 371 (c)(1),
(2), (4) Date: Nov. 7, 2013

(87) PCT Pub. No.: WO2012/118173
PCT Pub. Date: Sep. 7, 2012

(65) Prior Publication Data
US 2014/0066644 A1    Mar. 6, 2014

(30) Foreign Application Priority Data
Mar. 3, 2011 (JP) ................... 2011-046621

(51) Int. Cl.
*A23D 9/00* (2006.01)
*C11C 1/00* (2006.01)
(Continued)

(52) U.S. Cl.
CPC . *C11B 3/003* (2013.01); *C11B 3/12* (2013.01); *A23D 9/007* (2013.01); *A23D 9/04* (2013.01); *C11B 3/001* (2013.01); *C11B 1/025* (2013.01); *C11C 3/08* (2013.01); *C11C 1/002* (2013.01); *C11C 1/10* (2013.01); *C11C 3/00* (2013.01); *C12P 7/6472* (2013.01)

(58) Field of Classification Search
USPC .......................................... 554/224; 435/271
See application file for complete search history.

(56) References Cited

U.S. PATENT DOCUMENTS

| | | |
|---|---|---|
| 4,804,555 A | 2/1989 | Marschner et al. |
| 6,166,230 A | 12/2000 | Bijl et al. |

(Continued)

FOREIGN PATENT DOCUMENTS

| | | | |
|---|---|---|---|
| EP | 2172558 A1 | * | 4/2010 |
| JP | 3-500054 A | | 1/1991 |

(Continued)

OTHER PUBLICATIONS

International Search Report for International Application No. PCT/JP2012/055334; Date of Mailing: Jun. 5, 2012, with English Translation.

(Continued)

*Primary Examiner* — Deborah D Carr
(74) *Attorney, Agent, or Firm* — Cantor Colburn LLP (57) ABSTRACT

A method for lowering content of a sterol in a highly unsaturated fatty acid-concentrated oil in a method to concentrate a highly unsaturated fatty acid by using a lipase reaction, may include removing the free form of the sterol from a raw material oil that includes a highly unsaturated fatty acid-containing glyceride prior to performing the lipase reaction; and thereafter concentrating the highly unsaturated fatty acid in the glyceride by using a lipase that is less reactive for the highly unsaturated fatty acid.

19 Claims, 6 Drawing Sheets

(51) Int. Cl.
    *C11B 3/00*    (2006.01)
    *C11B 3/12*    (2006.01)
    *A23D 9/007*   (2006.01)
    *A23D 9/04*    (2006.01)
    *C11B 1/02*    (2006.01)
    *C11C 3/08*    (2006.01)
    *C11C 1/10*    (2006.01)
    *C11C 3/00*    (2006.01)
    *C12P 7/64*    (2006.01)

(56) References Cited

U.S. PATENT DOCUMENTS

| | | |
|---|---|---|
| 7,678,930 B2 | 3/2010 | Sondbo et al. |
| 2005/0287651 A1 | 12/2005 | Akimoto et al. |
| 2009/0176284 A1 | 7/2009 | Furihata et al. |

FOREIGN PATENT DOCUMENTS

| | | |
|---|---|---|
| JP | 03-259999 A | 11/1991 |
| JP | 04-016519 A | 1/1992 |
| JP | 2000-510513 A | 8/2000 |
| JP | 2006-501840 A | 1/2006 |
| WO | 2004007654 A1 | 1/2004 |
| WO | 2004007655 A1 | 1/2004 |
| WO | WO 2004007654 A1 * | 1/2004 |
| WO | WO 2004007655 A1 * | 1/2004 |
| WO | 2004043894 A1 | 5/2004 |
| WO | 2007119811 A1 | 10/2007 |

OTHER PUBLICATIONS

European Search Report corresponding to Application No. 12752142.5-1357/2682453, Mailing date: Jul. 10, 2014, 7 pages.

* cited by examiner

METHOD FOR PRODUCING OIL CONTAINING HIGHLY UNSATURATED FATTY ACID USING LIPASE

This is the U.S. national stage of application No. PCT/JP2012/055334, filed on 2 Mar. 2012. Priority under 35 U.S.C. §119(a) and 35 U.S.C. §365(b) is claimed from Japanese Application No. 2011-046621, filed 3 Mar. 2011, the disclosure of which is also incorporated herein by reference.

TECHNICAL FIELD

The present invention relates to a method for producing oil containing highly unsaturated fatty acid using lipase reactions. Specifically, the present invention relates to a method for producing oil containing highly unsaturated fatty acid that contains a reduced amount of cholesterol.

BACKGROUND ART

In addition to being nutrients that are essential for growth of vertebrates, including humans, highly unsaturated fatty acids in recent years have been frequently reported to be involved in cardiovascular diseases and inflammatory diseases. There have been many reports of findings that the intake of n-3 type highly unsaturated fatty acids, such as docosahexaenoic acid and eicosapentaenoic acid, is particularly useful for human health. There have been reports that the ratio of intake amount of n-3 type highly unsaturated fatty acid to intake amount of n-6 type highly unsaturated fatty acid is important. Today's society is characterized in that there are trends for the increased ingestion of calories, cholesterol, and n-6 type highly unsaturated fatty acids, and there is a trend for decreased ingestion of n-3 type highly unsaturated fatty acids. These trends have come to be considered to be related to various types of adult-onset diseases or the like.

Fish oil is an oil that is rich in n-3 type highly unsaturated fatty acids. The intake of such fish oil is widely recommended, and methods are being devised for the concentration of the n-3 type highly unsaturated fatty acids in fish oil for more efficient intake of n-3 type highly unsaturated fatty acids. The concentration of highly unsaturated fatty acids using lipase reactions is one such method.

Lipases are enzymes that catalyze hydrolysis reactions to decompose oils into free fatty acids and glycerin. Various types of animals and plants and microorganisms are known to have lipases. A kind of the lipases does not necessarily have the same effect on all fatty acids. Differences in the activity of lipases occur due to bonding position within the glyceride, carbon chain length of the fatty acid, number of double bonds, or the like. It is thus possible to selectively hydrolyze fatty acids using such lipases, and as a result, it becomes possible to concentrate a specific fatty acid within the glyceride fraction. For example, when a lipase produced by a kind of the genus *Candida* is used, it is known that hydrolysis reaction of fish oil results in concentration of highly unsaturated fatty acids, such as docosahexaenoic acid, in the undecomposed glyceride fraction (Patent Document 1).

Hydrolysis reaction by lipase in this manner is a method that is effective for the concentration of highly unsaturated fatty acids. The concentration of highly unsaturated fatty acid in the glyceride fraction increases with progress of hydrolysis with respect to fatty acids other than those of the target highly unsaturated fatty acid.

Although attention is paid to the ingestion of oils just like the ingestion of triglycerides, the cholesterol content is also important. The excessive ingestion of cholesterol is thought to result in the ready occurrence of arterial sclerosis and cardiac infarction, and thus such excessive ingestion is thought to be undesirable. In addition to triglycerides, the raw fish oils and microbial oils that contain highly unsaturated fatty acids also include cholesterol.

In Patent Document 2, a method for adding a volatile working fluid and for use of distillation for removal of the free form of cholesterol from an oil containing highly unsaturated fatty acid is described.

CITATION LIST

Patent Documents

Patent Document 1: Japanese Examined Patent Application Publication No. H4-16519
Patent Document 2: U.S. Pat. No. 7,678,930

SUMMARY OF INVENTION

Technical Problem

Various methods have been investigated for the production of oils that contain highly unsaturated fatty acids using lipase reactions as described above. However, the present invention is focused on sterols, particularly, cholesterol, contained in the highly unsaturated fatty acid-enriched oil produced by the lipase reaction. A concentrated highly unsaturated fatty acid-enriched oil is used with the goal of ingestion of useful components such as docosahexaenoic acid (sometimes referred to hereinafter as "DHA"), eicosapentaenoic acid (sometimes referred to hereinafter as "EPA"), or arachidonic acid (sometimes referred to hereinafter as "ARA"). When such oils or fats are ingested, it is thought the content of untargeted or undesirable cholesterol is preferably as low as possible. The problem for the present invention is to provide a highly unsaturated fatty acid-enriched oil that has a lower content of cholesterol.

Solution to Problem

While investigating whether or not there might be leeway for attempting further improvement concerning highly unsaturated fatty acid-enriched oils produced by lipase reaction, the inventors of the present invention achieved the present invention by the discovery that the lowering of cholesterol included in highly unsaturated fatty acid-enriched oils produced by lipase reaction was unexpectedly difficult.

The gist of the present invention is the method of producing a highly unsaturated fatty acid-containing glyceride, and a highly unsaturated fatty acid-containing glyceride of the below listed (1) to (19).

(1) A method for lowering content of a sterol in a highly unsaturated fatty acid-enriched oil in a method to concentrate a highly unsaturated fatty acid by using a lipase reaction, which comprises the steps of: removing the free form of the sterol from a raw material oil that includes a highly unsaturated fatty acid-containing glyceride prior to performing the lipase reaction; and thereafter concentrating the highly unsaturated fatty acid in the highly unsaturated fatty acid-containing glyceride by using a lipase that is less reactive for the highly unsaturated fatty acid.

(2) The method according to (1), wherein the sterol is cholesterol.

(3) A method for producing a highly unsaturated fatty acid-containing glyceride using the method described in (2), wherein the content of the cholesterol in the glyceride is 0.3 weight % or less, and the content of the highly unsaturated fatty acid in the fatty acids of the glyceride is 40 area % or more.

(4) The method for producing a highly unsaturated fatty acid-containing glyceride according to (3), wherein the lipase reaction is performed at a temperature of 25° C. or below; the content of the cholesterol in the glyceride is 0.3 weight % or less, the content of the highly unsaturated fatty acid in the glyceride is 40 area % or more; and the proportion of saturated fatty acids in the glyceride is 12 area % or less.

(5) The method according to (3) or (4), wherein the lipase is derived from a microbe selected from the group consisting of: *Candida cylindracea*, *Alcaligenes* sp., *Burkholderia cepacia*, *Pseudomonas fluorescens*, *Thermomyces lanuginosa*, *Rhizomucor miehei*, and *Pseudomonas* sp.

(6) The method according to any one of (3) to (5), wherein the cholesterol is removed by a distillation process.

(7) The method according to (6), wherein the distillation process is performed at a temperature of from 200 to 270° C.

(8) The method according to (6), wherein the distillation process is performed at a temperature of from 220 to 260° C.

(9) The method according to (6), wherein the distillation process is performed at a pressure of 5 Pa or less.

(10) The method according to (6), wherein the distillation process is performed at a pressure of 2 Pa or less.

(11) The method according to (6), wherein a flux rate of the distillation process is from 20 to 200 $(kg/h)/m^2$.

(12) The method according to (6), wherein a flux rate of the distillation process is from 20 to 150 $(kg/h)/m^2$.

(13) The method according to any one of (6) to (12), wherein the distillation process is a distillation method selected from the group consisting of thin film distillation, molecular distillation, and short path distillation or a combination thereof.

(14) The method according to any one of (3) to (13), wherein the highly unsaturated fatty acid is selected from the group consisting of docosahexaenoic acid (DHA), eicosapentaenoic acid (EPA), arachidonic acid (ARA), and dihomo-γ-linolenic acid (DGLA).

(15) The method according to (14), wherein the raw material oil is selected from the group consisting of fish oils and microbial oils.

(16) A highly unsaturated fatty acid-containing glyceride, wherein the content of sterol is 0.3 weight % or less, and the content of highly unsaturated fatty acid is 40 area % or more.

(17) The glyceride according to (16), wherein the sterol is cholesterol.

(18) The glyceride according to (16) or (17), wherein the proportion of saturated fatty acids in the fatty acids is 12 area % or less.

(19) The glyceride of any one of (16) to (18), wherein proportion of triglyceride in the glyceride is not less than 80 area %.

(20) The glyceride according to any one of (16) to (19), wherein the highly unsaturated fatty acid is at least one type selected from the group consisting of docosahexaenoic acid (DHA), eicosapentaenoic acid (EPA), arachidonic acid (ARA), and dihomo-γ-linolenic acid (DGLA).

The expression "area %" in the present invention indicates the content proportion of a peak of a component as the ratio relative to the total peak area of all peak areas of the various components in an analytical graph using gas chromatography or thin-layer chromatography/flame ionization detector (TLC/FID) of a mixture of glyceride ingredients composed of various types of fatty acids. The fatty acid composition was determined by gas chromatography by the method indicated in the working examples. The lipid composition was determined using TLC/FID. In the field of oil chemistry, "area %" is used with nearly the same meaning as "weight %".

Advantageous Effects of Invention

According to the method of the present invention, the highly unsaturated fatty acid such as EPA or DHA may be concentrated, and a glyceride may be produced that has a low cholesterol content. When the highly unsaturated fatty acid beneficial for health is ingested, it is possible to lower the ingested amount of superfluous cholesterol, and it is further possible to lower the ingested amount of saturated fatty acids.

DESCRIPTION OF EMBODIMENTS

The present invention is a method for lowering content of a sterol in a highly unsaturated fatty acid-concentrated oil in a method to concentrate a highly unsaturated fatty acid using a lipase reaction including the steps of: removing the free form of the sterol from a raw material oil that includes a highly unsaturated fatty acid-containing glyceride prior to performing the lipase reaction; and thereafter concentrating the highly unsaturated fatty acid in the highly unsaturated fatty acid-containing glyceride by using a lipase of less reactive for the highly unsaturated fatty acid.

The following is a detailed explanation of the invention. In the present invention, the expression "highly unsaturated fatty acid" refers to a fatty acid having at least 18 carbons and 3 or more double bonds, further preferably having at least 20 carbons and 3 or 4 or more double bonds, and most preferably having at least 20 carbons and 5 or more double bonds. Such fatty acids are exemplified by α-linolenic acid (18:3, n-3), γ-linolenic acid (18:3, n-6), dihomo-γ-linolenic acid (20:3, n-6), arachidonic acid (20:4, n-6), eicosapentaenoic acid (20: 5, n-3), docosapentaenoic acid (22:5, n-6), docosahexaenoic acid (22:6, n-3), or the like. These highly unsaturated fatty acids are known to be contained in large amounts in certain microorganism oils, plant oils, marine animal oils, or the like. Such highly unsaturated fatty acids are exemplified by: marine animal oils such as those of fishes including sardine, tuna, bonito, and the like and crustaceans including krill and the like; plant oils such as perilla oil, flaxseed oil, soybean oil, and rapeseed oil; and oils produced by microorganisms belonging to the genera *Mortierella, Penicillium, Aspergillus, Rhodotorula, Fusarium*; or the like.

Cholesterol is a compound that has a steroid backbone structure and is indicated by the molecular formula $C_{27}H_{46}O$. Cholesterol is present in natural products in the free form or ester form. Acyl cholesterol is an ester form of cholesterol where a fatty acid is bonded to the hydroxy group (OH group) part.

The glycerides containing highly unsaturated fatty acids of the present invention are triglycerides, diglycerides, and monoglycerides containing as constituent fatty acids the aforementioned highly unsaturated fatty acids. The aforementioned microorganism oils, plant oils, and marine animal oils comprise, as main components, triglycerides containing highly unsaturated fatty acids.

Any lipase may be used for the present invention as long as the lipase that is less reactive for highly unsaturated fatty acid and has the property of concentrating highly unsaturated fatty acid in the undecomposed glyceride fraction by a hydrolysis reaction or alcoholysis reaction. Such lipases are exemplified by lipases obtained from microorganisms belonging to *Alcaligenes* sp. (Lipase QLM, Lipase QLC, Lipase PL, all produced by Meito Sangyo Co., Ltd.), lipases obtained from microorganisms belonging to *Burkholderia cepacia* (Lipase PS, produced by Amano Enzyme Inc.), lipases obtained from microorganisms belonging to *Pseudomonas fluorescens* (Lipase AK, produced by Amano Enzyme Inc.), lipases obtained from microorganisms belonging to *Thermomyces lanuginosa* (Lipozyme TLIM, produced by Novozymes), or the like. Lipase derived from *Candia rugose* concentrates DHA, arachidonic acid, and γ-linolenic acid. Lipase derived from *Rhizomucor miehei* has the ability to concentrate DHA. Lipase derived from *Pseudomonas* sp. has the ability to concentrate EPA. All of these lipases are commercially marketed and may be readily obtained. As may be required, these lipases may be immobilized prior to use. Preferably, the utilized lipase may be derived from *Candida cylindracea*, i.e. a lipase derived from the genus *Candida*. Lipase derived from *Candida cylindracea* is exemplified by Lipase OF, produced by Meito Sangyo Co., Ltd.

Although no particular limitation is placed on the utilized amount of the lipase. If a powdered lipase is used, at least 10 units of lipase per gram of oil or fat are preferably utilized, and in consideration of a practical reaction rate, at least 30 units of lipase are preferably utilized per gram of oil or fat. If a fixed lipase is used, the amount of immobilized lipase relative to the oil or fat is preferably at least 0.01% (w/w). The utilized amount of genus *Candida*-derived lipase is normally from 10 to 2,000 units per 1 g of triglyceride, and preferably is from 200 to 700 units per 1 g of triglyceride. Here, 1 unit is the amount of enzyme that releases 1 μmol of fatty acid in 1 minute. The hydrolysis reaction using lipase requires that the reaction be performed in the presence of a sufficient amount of water for expression of the hydrolysis activity of lipase.

The amount of water present per 1 part by weight of triglyceride is from 10 to 200 parts by weight, and preferably is from 30 to 60 parts by weight.

The lipase reaction may be performed by methods such as those described in WO2007/119811, for example.

In order to suppress deterioration of the fatty acids, deactivation of the enzyme, or the like, the hydrolysis is preferably performed under an inert gas atmosphere, such as dry nitrogen. An antioxidant may preferably also be used, such as tocopherol, ascorbic acid, or t-butyl hydroquinone.

Any temperature may be used for the hydrolysis reaction as long lipase activity is present at that temperature. This temperature is preferably from 10 to 40° C. In order to suppress the amount of saturated fatty acid, the hydrolysis reaction is performed at a temperature of 25° C. or below, preferably from 10 to 25° C., and further preferably from 15 to 20° C. Although as low a temperature as possible is preferred for causing a lowering of the content of saturated fatty acids, at temperatures of not more than 10° C., the viscosity of the oil increases and the rate of the enzyme reaction itself declines excessively. Thus, a temperature of roughly from 15 to 20° C. is most preferable. In the case of a large-scale reaction, the reaction phase temperature is preferably set to be from an average of from 15 to 20° C., and the reaction may be performed while maintaining temperature within a range of about ±5° C. The hydrolysis reaction is performed in a flow or the like caused by stirring, injecting an inert gas or the like.

Hydrolysis is performed until the proportion of the highly unsaturated fatty acid (e.g. docosahexaenoic acid) contained in the constituent fatty acids reaches the target value. Reaction conditions differ according to the raw material oil. For example, in the case of using tuna oil (containing about 23% DHA) as the raw material, the reaction time is preferably at least 7 hours, and normally hydrolysis is performed for 5 to 24 hours. The proportion of docosahexaenoic acid then becomes not less than 40 area %, preferably not less than 46 area %, by a single lipase reaction. Moreover, acid value may be used as an indicator showing the degree of hydrolysis. The proportion of docosahexaenoic acid normally becomes at least 46 area % when the acid value becomes not less than 140.

By performing hydrolysis in this manner, a mixture of hydrolysate and unreacted triglyceride is obtained as the reaction liquid. Hydrolysis of the ester bond between glycerin and docosahexaenoic acid is difficult for lipases derived from the genus *Candida*, and thus the proportion of docosahexaenoic acid in the constituent fatty acids in unreacted triglycerides and partial glycerides within the reaction solution increases as hydrolysis progresses. By the time this hydrolysis has been completed, docosahexaenoic acid is concentrated so that this proportion of docosahexaenoic acid is 40 area % or more, and preferably is 46 area % or more. On the other hand, most of the free fatty acids are fatty acids other than the docosahexaenoic acid.

After completion of the hydrolysis, the oil layer of the reaction liquid is obtained by removing the aqueous layer containing lipase, glycerin, and the like via centrifugal separation or the like. Then, the free fatty acids are removed. Methods that may be adopted for the separation and removal of the free fatty acids include known methods such as the method of removal as alkaline salts, method using a liquid chromatographic device, fractional distillation method, and crystal separation method. However, molecular distillation and steam distillation are preferred.

By removal of the free fatty acid, a glyceride mixture is obtained of partial glycerides and triglycerides containing docosahexaenoic acid at high concentration.

During production of a highly unsaturated fatty acid-concentrated oil by lipase reaction in the aforementioned manner, the inventors of the present invention noticed that cholesterol remains in the glyceride fraction without being removed with the free fatty acids, i.e. the resultant cholesterol content proportion in the highly unsaturated fatty acid-concentrated oil is higher than the cholesterol content proportion in the raw material oil. Thus, the removal of cholesterol after the lipase reaction was attempted. However, the cholesterol had undergone esterification by the lipase reaction, and removal was not possible without use of an atypical method.

The performance of cholesterol removal prior to performing the lipase reaction is a necessary step of the method of the present invention. This step is required since performance of the lipase reaction results in esterification of the free form of cholesterol included in the raw material oil to produce the esterified form of cholesterol so that separation from the glyceride becomes difficult.

Tuna fish oil or the like, for example, which contains a high amount of DHA, is used as the raw material oil for a DHA-concentrated glyceride. Unrefined tuna fish oil that has been refined by undergoing deacidification and decolorization or the like may be used as the raw material oil in the present invention. Although the content of cholesterol in unrefined tuna fish oil is about 0.5 weight %, the content of cholesterol becomes about 0.18 weight % after deacidification with alkaline. However, if the free fatty acids are removed after performing the lipase reaction, cholesterol becomes concentrated in addition to the unsaturated fatty acids. As a matter of practice, when DHA is concentrated to a content 40 area % or more, the cholesterol becomes concentrated about 2- to 3-fold.

According to the method of the present invention, by removal of the cholesterol prior to the lipase reaction, it is possible to obtain a concentrated oil that has a cholesterol content 0.3 weight % or less, and further 0.2 weight % or less.

According to the present invention, the deacidified and decolorized raw material oil is subjected to a distillation process, and the cholesterol is removed. Thereafter, the aforementioned lipase reaction is used.

Removal of cholesterol according to the present invention is performed by a distillation process. The distillation process is performed as one type of distillation or multiple types of distillation selected from the group consisting of thin film distillation, molecular distillation, and short path distillation (SPD). Since the time at high temperature is short, these distillation methods are suitable for distillation of oils containing highly unsaturated fatty acids.

The distillation process is preferably performed at a flux rate of from 20 to 200 (kg/h)/m$^2$, a temperature of from 200 to 270° C., and a pressure of 5 Pa or less. The distillation process is further preferably performed at a flux rate of from 20 to 200 (kg/h)/m$^2$, a temperature of from 220 to 260° C., and a pressure of 2 Pa or less. Productivity declines when the flux rate is excessively low. Therefore, while confirming the removal of cholesterol, the maximum flow is preferably used within a range capable of removal of cholesterol.

Molecular distillation refers to distillation performed at high vacuum (i.e. less than 0.1 Pa) fixed pressure using a condenser arranged within a distance shorter than roughly the mean free path of vapor molecules vaporized from the heating surface. Short path distillation was developed in order to increase the distillation capacity of molecular distillation. Short path distillation is performed at a pressure in the intermediate vacuum region (higher than 0.1 Pa), and since the condenser is disposed at roughly the same distance as the mean free path of the vapor molecules, short path distillation is a practical method that has greatly improved distillation capacity in comparison to molecular distillation.

Short path distillation is particularly suitable for distillation equipment used at the scale of actual production.

According to the production method of the present invention, it is possible to obtain a highly unsaturated fatty acid-containing glyceride that has a cholesterol content of 0.3 weight % or less, or that further has a cholesterol content of 0.2 weight % or less. According to the production method of the present invention, it is possible to obtain a highly unsaturated fatty acid-containing glyceride that has a highly unsaturated fatty acid content of 40 area % or more.

Further, by performing the lipase reaction at low temperature, it is possible to concentrate the docosahexaenoic acid to a concentration of 40 area % or more, and to obtain a glyceride that has a total saturated fatty acid content of 12 area % or less, and preferably 10 area % or less. Particularly, the concentration of palmitic acid (having 16 carbons), which is contained at the highest concentration among saturated fatty acids, is not more than 8 area %, and preferably is not more than 6 area %. When the lipase reaction is performed at low temperature, it is possible to obtain a high proportion of triglycerides in the glyceride lipid composition in the obtained reaction oil. If an oil is used as the raw material oil that contains a large amount of docosahexaenoic acid such as the refined tuna fish oil or refined bonito fish oil indicated in the production examples, although a level of about 70 area % was obtained at 40° C., a level 80 area % or more was obtained by low temperature reaction. The present invention is capable of obtaining a glyceride that has a triglyceride proportion in the glycerides that is 80 area % or more.

By performing deacidification, decoloration, and deodorizing treatment of the lipase reaction oil of the present invention, highly unsaturated fatty acids are concentrated, and a glyceride may be obtained that has a reduced content of cholesterol. Any method may be used for the deacidification, decoloration, and deodorization. Deacidification treatment is exemplified by distillation processing. Decolorizing treatment is exemplified by treatment using activated white earth, activated carbon, silica gel, or the like. Deodorizing treatment is exemplified by steam distillation or the like.

Monoglycerides are simultaneously removed during deacidification treatment by distillation, and it is thus possible to further increase the proportion of triglycerides in the obtained oil. It is possible to obtain a proportion of triglyceride in the glycerides that is 85 area % or more, and preferably is 90 area % or more.

The method of the present invention may be used for reduction of sterols that are present in both the free form and ester form, and may be used for non-cholesterol sterols. That is to say, this is a method for producing a highly unsaturated fatty acid-containing glyceride that is characterized in that the method includes the steps of: in a method to concentrate a highly unsaturated fatty acid removing the free form of the sterol from a raw material oil that includes a highly unsaturated fatty acid-containing glyceride prior to performing a lipase reaction; and thereafter using a lipase of less reactive for highly unsaturated fatty acids to concentrate the highly unsaturated fatty acid within the highly unsaturated fatty acid-containing glyceride. This method produces a highly unsaturated fatty acid-containing glyceride in which the sterol content is 1 weight % or less, and preferably is 0.3 weight % or less, and in which the highly unsaturated fatty acid content is 40 area % or more, and preferably is 60 area % or more. When arachidonic acid, dihomo-γ-linolenic acid, or the like has been produced by a microorganism, this method is suitable for removal of whatever sterol is inherent to the particular microorganism, e.g. desmosterol, 24,25-methylenecholest-5-en-3β-ol, or the like.

EXAMPLES

The present invention will now be explained in greater detail through the use of working examples, but is in no way limited to these working examples.

Measurements of cholesterol, fatty acid composition and acid value were performed by the below described methods for each of the working examples.

Measurement of Cholesterol

The total cholesterol content (free cholesterol plus cholesterol esters), free cholesterol content, and cholesterol ester content in the oil were measured by gas chromatography.

The measurement of total cholesterol was performed in the following manner.

1 mL of 0.1 g/L 5α-cholestane as an internal standard substance was added to about 0.1 g of the oil. Then, 1 mL of a 2 mol/L potassium hydroxide solution in water-containing ethanol was added, and the mixture was then heated for 10 minutes at 100° C. After the mixture was cooled down, 3 mL of petroleum ether and 3 mL of saturated ammonium sulfate were added, and the mixture was stirred and then allowed to sit. Thereafter, the upper layer was recovered and analyzed by gas chromatography. In order to determine the relative sensitivity values for 5α-cholestane and free cholesterol, a hexane solution containing 25 mg each of dissolved 5α-cholestane and cholesterol was analyzed by gas chromatography, and the total cholesterol content was calculated.

The free cholesterol content and cholesterol ester content were measured in the following manner.

About 1.0 g of oil was dissolved in 10 mL of hexane, and 0.5 mL of this solution was sampled. This was loaded into a silica gel cartridge (Waters Associates, Sep-pack Plus Silica Cartridge™ 55-105 µm) and was eluted using 5 mL of hexane:diethyl ether (9:1 volume ratio) to produce the cholesterol ester fraction. A further 5 mL of diethyl ether was fed through the cartridge to produce the free cholesterol fraction. Thereafter, the solvent was removed by distillation, and then the same procedure was used as that of the total cholesterol content measurement. The proportions of cholesterol ester and free cholesterol were found, and the respective concentrations were calculated using the total cholesterol value.

Gas Chromatography Analysis Conditions
Equipment type: Agilent 6890 GC system (Agilent Technologies, Inc.)
Column: DB-wax J & W 123-1012
Column temperature: 270° C.
Injection temperature: 300° C.
Injection method: split
Split ratio: 50:1
Detector temperature: 300° C.
Detector: FID
Carrier gas: helium (39.3 kPa, constant pressure)

Measurement of Fatty Acid Composition

The composition of the fatty acids of fish oil used as the raw material and fish oil which was deacidified by short path distillation, were measured by ethyl esterification of the fish oil and then gas chromatography. That is to say, 1 mL of 1N sodium ethylate in ethanol solution was added to 40 µL of fish oil, and the mixture was stirred for about 30 seconds. Thereafter, 1 mL of 1N hydrochloric acid was added to neutralize the mixture, and 2 mL of hexane and 3 mL of saturated ammonium sulfate aqueous solution were added. After stirring and then allowing the mixture to sit, content of the supernatant was measured by gas chromatography.

The glyceride fraction fatty acid composition of the oil after the enzyme reaction was measured by ethyl esterification of the glyceride fraction, removal of free fatty acids (i.e. byproduct of the enzyme reaction), and measurement by gas chromatography. That is to say, 1 mL of 1N sodium ethylate in ethanol solution was added to 100 (70) µL of reaction oil, and the mixture was stirred for about 30 seconds. Thereafter, 1 mL of 1N hydrochloric acid was added to neutralize the mixture, and 1 (0.7) mL of hexane and 3 mL of saturated ammonium sulfate aqueous solution were added. After stirring and then allowing the mixture to sit, the supernatant containing ethyl esters and free fatty acids was collected. In order to remove the free fatty acids from the obtained supernatant, 1 or 2 drops of triethylamine was added to 250 (700) µL of the supernatant, and then the mixture was fed to a silica gel column (Varian Inc., Bond Elut SI, 100 mg, 1 mL). The ethyl esters were eluted using 750 (1,000) µL of a mixed solution of hexane and ethyl acetate (hexane:ethyl acetate=50:1 volume ratio), and this eluate was measured by gas chromatography (these are the quantities used in these working examples; the quantities within parentheses within the above text were used for measurement in the production examples).

Gas Chromatography Analysis Conditions
Equipment type: Agilent 6850 GC system (Agilent Technologies, Inc.)
Column: DB-wax J & W 122-7032
Column temperature: 200° C.
Injection temperature: 300° C.
Injection method: split
Split ratio: 30:1 (split ratio was 50:1 in the production examples)
Detector temperature: 300° C.
Detector: FID
Carrier gas: helium (2.9 mL/min, constant flow)

Measurement of Acid Value (AV)

For fish oil used as the raw material and fish oil from which free fatty acid was separated by deacidification treatment with short path distillation, the measurement was processed in the below described manner.

About 1.5 g of oil was dissolved in ethanol-diethyl ether mixed solvent (1:1, volume ratio), and 1 drop of phenolphthalein was added. Then the mixture was neutralization-titrated using 0.1N sodium hydroxide/ethanol solution, and acid value was calculated based on the following formula.

$$AV = \text{titration amount (mL)} \times 5.611/\text{sample mass (g)}$$

The oil that had been subjected to enzyme reaction was treated in the below described manner.

About 0.5 g of oil was dissolved in ethanol, a drop of phenolphthalein was added, and neutralization-titration was performed using a 1N sodium hydroxide aqueous solution. The acid value was calculated based on the following formula.

$$AV = \text{titration amount (mL)} \times 56.11/\text{sample mass (g)}$$

Measurement of Lipid Composition

Measurement of lipid composition was performed by thin-layer chromatography/flame ionization detector (TLC/FID, Iatroscan, Mitsubishi Kagaku Iatron, Inc.). 20 μL of oil was dissolved in 1 mL of hexane, and 0.5 μL of this solution was loaded into a Chromarod. A mixed solution of hexane, diethyl ether, and acetic acid (hexane:diethyl ether:acetic acid=70:30:0.1 volume ratio) was used as the development solvent (35 min development time). Analysis was performed using the Iatroscan.

Working Example 1

Sterols and fatty acids were removed by short path distillation from water-washed tuna oil. Short path distillation was performed using a short path distillation (SPD) KD450 (manufactured by UIC GmbH, 4.5 m² evaporation surface area) at 0.6 to 1.5 Pa vacuum, 250 to 260° C. temperature, and a feed rate of 200 kg/h (flux rate of 44.4 (kg/h)/m²).

330 mL of tuna oil that had been treated by short path distillation (refined fish oil A, produced by Nippon Suisan Kaisha, Ltd.), 165 mL of distilled water, and 275 mg of Lipase OF (produced by Meito Sangyo Co., Ltd., 300 unit/mL oil) were mixed, and the mixture was stirred for 30 h at 20° C. The reaction mixture was sampled at the start of the reaction, 10 h after start of the reaction, 23 h after start of the reaction, and 30 h after start of the reaction. Lipase in the sample was deactivated by heated at 80° C. for 10 minutes, and then a centrifuge was used to separate the sample into an oil layer and aqueous layer (40° C., 1800×g, 10 minutes), and the enzyme reaction oil was recovered.

The oil was sampled after 30 hours and was further deacidified by short path distillation. The utilized equipment was a short path distillation device KDL5 (manufactured by UIC GmbH, 0.05 m² evaporation surface area), and distillation conditions were 0.1 Pa vacuum, 200° C. body temperature, and 0.60 L/h feed rate.

The glyceride-contained fatty acid compositions (area %), acid values (AV), total cholesterol contents (weight %), cholesterol ester contents (weight %), and free cholesterol contents (weight %) of the refined fish oil A (raw material prior to reaction), the obtained enzyme reaction oil, and the distillative deacidification-treated oil, as well as the yield of distillative deacidification-treated oil (weight %), are shown in Table 1.

TABLE 1

|  | Acid value | DHA | Yield after deacidification treatment | Total cholesterol | Cholesterol esters | Free cholesterol |
| --- | --- | --- | --- | --- | --- | --- |
| Refined fish oil A (reaction raw material) | 0.2 | 25.1% | — | 0.05% | 0.04% | 0.01% |
| After 10 h of reaction | 106.4 | 44.0% | — | 0.06% | 0.05% | 0.01% |
| After 23 h of reaction | 114.4 | 47.4% | — | 0.05% | 0.04% | 0.01% |
| After 30 h of reaction | 118.5 | 48.3% | — | 0.05% | 0.04% | 0.01% |
| After deacidification treatment | 6.8 | 48.3% | 43.3% | 0.12% | 0.12% | 0.00% |

Comparative Example 1

Refined tuna fish oil (refined fish oil B, produced by Nippon Suisan Kaisha, Ltd.) was used that had been refined by the general refining method using phosphoric acid, sodium hydroxide, and activated earth (i.e. degumming, deacidification, and decoloring treatment, these are a refining method which do not remove sterols so that sterols remained). In the same manner as Working Example 1, oils were prepared after 10 h of reaction, after 23 h of reaction, after 30 h of reaction, and after deacidification treatment.

The fatty acid compositions (area %) in the glycerides and acid values for the refined fish oil B (pre-reaction raw material), the obtained enzyme reaction oil, and the post-distillative deacidification oil, as well as the yield of distillative deacidification-treated oil, are shown in Table 2.

TABLE 2

|  | Acid value | DHA | Yield after deacidification treatment | Total cholesterol | Cholesterol esters | Free cholesterol |
| --- | --- | --- | --- | --- | --- | --- |
| Refined fish oil B (reaction raw material) | 0.2 | 25.3% | — | 0.34% | 0.07% | 0.27% |
| After 10 h of reaction | 101.1 | 44.4% | — | 0.36% | 0.22% | 0.14% |
| After 23 h of reaction | 114.5 | 47.7% | — | 0.34% | 0.24% | 0.10% |
| After 30 h of reaction | 119.5 | 48.7% | — | 0.33% | 0.24% | 0.09% |
| After deacidification treatment | 7.1 | 48.4% | 42.9% | 0.48% | 0.46% | 0.02% |

Figure 1:
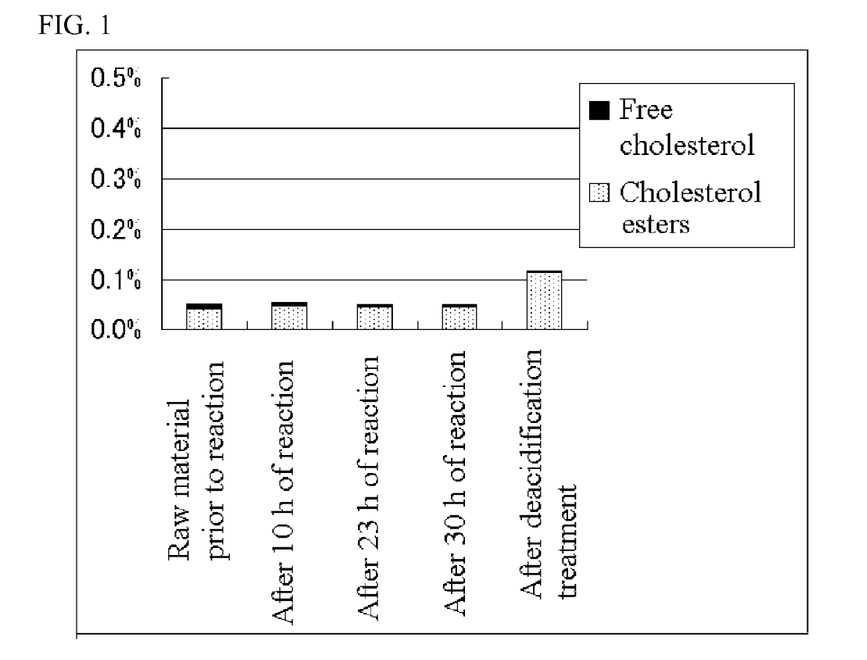
FIG. 1 is a graph showing change of cholesterol content during enzyme reaction and distillative deacidification of refined fish oil A in Working Example 1.
Figure 2:
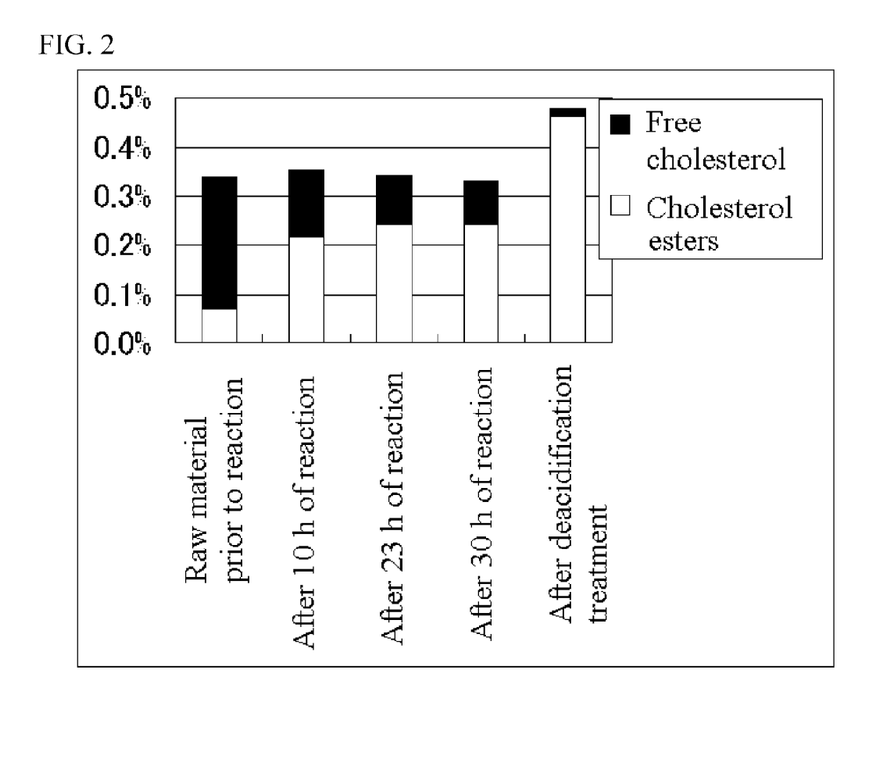
FIG. 2 is a graph showing change of cholesterol content during enzyme reaction and distillative deacidification of refined fish oil B in Comparative Example 1.

The cholesterol content in the oil of the aforementioned Working Example 1 is shown in FIG. 1, and the cholesterol content in the oil of the aforementioned Comparative Example 1 is shown in FIG. 2. Due to removal of free fatty acids, there was a relative increase in cholesterol content for both the deacidification-treated Working Example 1 and Comparative Example.

When Working Example 1 and Comparative Example 1 are compared, most of the cholesterol esters remained after the final distillative deacidification treatment of the Working Example 1, which used distillative deacidified refined fish oil A as the raw material, and the free cholesterol content was low in the pre-reaction raw material. Thus, there was little generation of cholesterol esters by the enzyme reaction, and as a result, the remnant total sterol content was low. On the other hand, there was considerable free cholesterol in the pre-reaction raw material of Comparative Example 1, which used refined fish oil B as a raw material that had undergone general refining rather than distillative deacidification. This free cholesterol became cholesterol esters due to the enzyme reaction, and most of the cholesterol esters remained after distillative deacidification treatment. It is understood that therefore a large amount of cholesterol esters remained in the oil after the final distillative deacidification.

Working Example 2

Sardine raw oils of various quality grades were used as the raw material oil, and short path distillation was performed while varying the distillation temperature. The utilized equipment was a short path distillation device KD10 (manufactured by UIC GmbH, 0.1 m$^2$ evaporation surface area), and distillation conditions were 1.0 to 1.4 Pa vacuum and 10 kg/h feed rate using the temperature indicated in Table 3 (181 to 250° C.).

Figure 3:
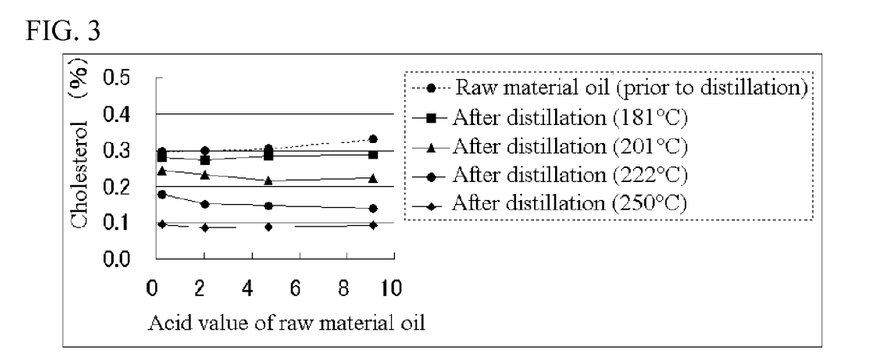
FIG. 3 is a graph showing change of total cholesterol content before and after each distillation of the raw material oil of Working Example 2.

The cholesterol contents (weight %) of the raw material oil and the oil after distillation are shown in Table 3 and FIG. 3. Quality of the utilized raw material sardine oils is indicted by acid value. It was possible to decrease cholesterol as the distillation temperature was increased, whatever the quality of the raw material oil. When the distillation temperature is 220° C. or higher, it is possible to reliably decrease acid value to 0.2 or less. Although there is relative increase of the cholesterol concentration in the deacidification step after lipase treatment, by lowering cholesterol by 0.15 weight % beforehand by distillation, it is possible after deacidification to produce a highly unsaturated fatty acid-concentrated oil that had a cholesterol content 0.3 weight % or less. In particular, by distillation at 250° C., it is possible to produce a highly unsaturated fatty acid-concentrated oil that had a cholesterol content 0.2 weight % or less.

TABLE 3

|  | Sample 1 | Sample 2 | Sample 3 | Sample 4 |
|---|---|---|---|---|
| Acid value of raw material oil | 0.26 | 2.06 | 4.71 | 9.10 |
| Raw material oil (before distillation) | 0.30 | 0.30 | 0.30 | 0.33 |
| After distillation (181° C.) | 0.28 | 0.27 | 0.29 | 0.29 |
| After distillation (201° C.) | 0.24 | 0.23 | 0.22 | 0.22 |
| After distillation (222° C.) | 0.18 | 0.15 | 0.15 | 0.14 |
| After distillation (250° C.) | 0.10 | 0.08 | 0.09 | 0.09 |

Working Example 3

Sardine raw oil was used as the raw material oil, and short path distillation was performed while varying the distillation temperature. The utilized equipment was a short path distillation device KDL5 (manufactured by UIC GmbH, 0.05 m$^2$ evaporation surface area), and distillation conditions were 0.006 mbar (0.6 Pa) vacuum, 270° C. temperature, and 1.2 kg/h feed rate.

The cholesterol contents (weight %) of the raw material oil and the oil after distillation are shown in Table 4. It was possible to lower the cholesterol content also under these conditions.

TABLE 4

|  | Raw material oil | After distillation |
|---|---|---|
| Residual amount (weight %) |  | 92.1 |
| Distilled off amount (weight %) |  | 7.9 |
| Total cholesterol (weight %) | 0.54 | 0.13 |
| Acid value | 5.79 | 0.14 |

Working Example 4

The same processing as that of Working Example 1 and Comparative Example 1 was performed at the scale of actual production. That is to say, tuna fish oil was used as the raw material oil, and a comparison was made between the method of the invention of the present application (which performed refining in the following order: water wash→short path distillation→enzyme reaction→molecular distillation→decolorization→deodorization) versus the conventional method (which performed refining in the following order: degumming, deacidification, and decolorizing of the same raw material oil→enzyme reaction→molecular distillation→wintering→decolorization→deodorization).

3 different lots of raw material were used for production respectively by each method. The cholesterol contents of the products are shown in Table 5.

The cholesterol content of tuna fish raw material oil was about 0.3 to 0.5 weight %. When a DHA-concentrated oil was produced by the conventional method, there was a relative increase in the total cholesterol in comparison to the raw material oil. However, according to the method of the present invention, the cholesterol content was found to be able to be stabilized and decreased below that of the raw material oil

TABLE 5

|  |  | Total cholesterol | Ester form | Free form |
|---|---|---|---|---|
| Present invention | Lot 1 | 0.199 | 0.188 | 0.011 |
|  | Lot 2 | 0.202 | 0.189 | 0.014 |
|  | Lot 3 | 0.192 | 0.181 | 0.012 |
| Conventional method | Lot 1 | 0.552 | 0.493 | 0.059 |
|  | Lot 2 | 0.579 | 0.527 | 0.052 |
|  | Lot 3 | 0.611 | 0.561 | 0.050 |

The below production examples are lipase reaction production examples capable of reducing the proportion of saturated fatty acids. Oil after removal of cholesterol was used as the raw material. By performing the lipase reaction by these methods, it is possible to produce a highly unsaturated fatty acid-concentrated oil that has a low cholesterol content and low saturated fatty acid content.

Production Example 1

To 3 mL of refined fish oil 1 (deacidified tuna oil, Nippon Suisan Kaisha, Ltd.) were added 1.5 mL of water and 5 mg of Lipase OF (Meito Sangyo Co., Ltd., 600 units/mL oil). A magnetic stirrer was used to stir the mixture for 14 hours in a constant-temperature bath at from 10 to 60° C. After the 14 hours of stirring, about 2 mL of the reaction oil was sampled, and the lipase was deactivated by heating for 10 minutes at 80° C. Thereafter, the mixture was separated into an oil layer and aqueous layer using a centrifugal separator (40° C., 1,800 g, 10 min) to obtain the reaction oil.

The fatty acid composition (area %) and the acid value of the glyceride fraction of the obtained reaction oil, and the fatty acid composition of the refined fish oil 1 (area %) are shown in Table 6. The total of the myristic acid (C14:0), palmitic acid (C16:0), and stearic acid (C18:0) content (area %) in the glyceride fraction obtained during gas chromatography is indicated as the saturated fatty acid content (hereinafter, "saturated fatty acid content" described in the manufacturing examples is taken to mean this value).

At reaction temperatures of from 30 to 60° C., content of the saturated fatty acids was about 15%. In contrast, content of the saturated fatty acids was 11.40% at 25° C., was 9.36% at 20° C., was 7.74% at 15° C., and was 8.42% at 10° C. The content of saturated fatty acid decreased greatly when the reaction was performed at low temperature. There was a great decrease in the saturated fatty acid content at 10 to 25° C. Moreover, reaction rate deteriorated at 10° C. relative to the other temperature conditions, resulting in a low acid value (AV) of 113.9. However, under such conditions, the saturated fatty acid content was low (i.e. 8.42%), and acid value was greatly reduced relative to that under 40° C. conditions (acid value (AV) was 125.1) where the hydrolysis reaction proceeded further.

Figure 4:
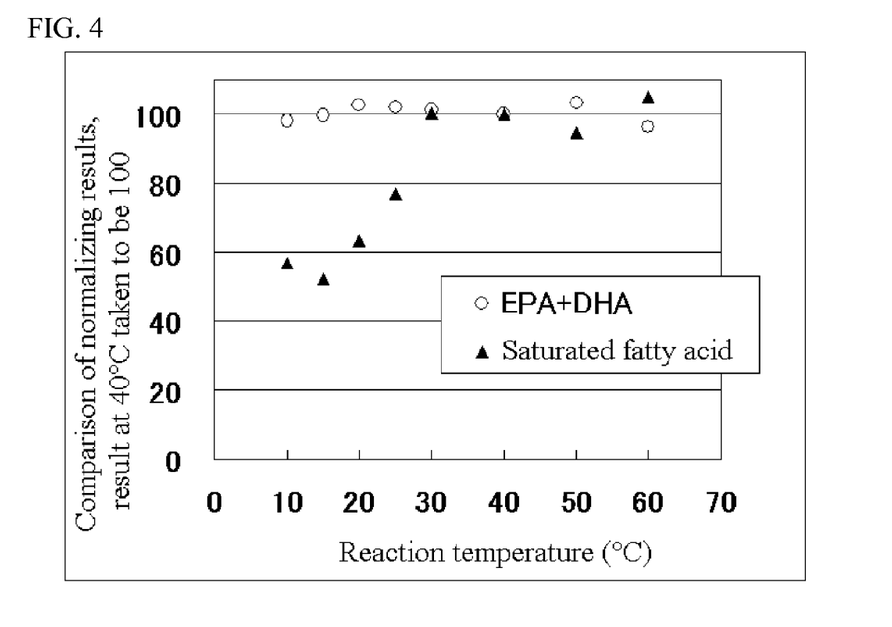
FIG. 4 is a graph showing proportions of saturated fatty acid and EPA+DHA contained in the glyceride fraction treated with lipase at each reaction temperature in Production Example 1, normalized such that results for the reaction at 40° C. are 100.

In order to compare the results of decrease of saturated fatty acids with those of the temperature range (near 40° C.) where the lipase hydrolysis reaction is generally carried out, the proportion of such fatty acid content at respective temperatures is shown in FIG. 4 where the total amount of DHA and EPA and the saturated fatty acid content at 40° C. are normalized to 100. From this chart, under 10 to 25° C. temperature conditions, it is understood that there was a great decrease in the saturated fatty acid content, while the EPA and DHA contents remained high.

Production Example 2

100 g of water and 320 mg of Lipase OF (Meito Sangyo Co., Ltd., 640 units/mL oil) were added to 200 g of refined fish oil 2 (deacidified tuna oil, Nippon Suisan Kaisha, Ltd.), and the mixture was stirred for 20 hours at from 10 to 40° C. using a blade-equipped agitator. After 20 hours of stirring, the reaction oil was heated to 80° C. for 15 min to deactivate lipase, and a supernatant reaction oil was obtained.

The fatty acid composition (area %) and the acid value of the glyceride fraction of the obtained reaction oil, and the fatty acid composition (area %) of the refined fish oil 2 are shown in Table 7 (only typical fatty acids are shown in the fatty acid composition). The glyceride content here was calculated by calculating the free fatty acid content equivalent to oleic acid from the acid value, and then subtracting the free fatty acid content from the total reaction oil. Moreover, the total of the myristic acid (C14:0), palmitic acid (C16:0), and stearic acid (C18:0) content (area %) in the glyceride fraction obtained during gas chromatography is indicated as the saturated fatty acid content.

In comparison to 35 and 40° C., there was a great decrease in the saturated fatty acid content at from 10 to 25° C.

TABLE 6

| | | Reaction temperature | | | | | | | | Refined |
|---|---|---|---|---|---|---|---|---|---|---|
| | | 10 | 15 | 20 | 25 | 30 | 40 | 50 | 60 | fish oil 1 |
| Fatty acid composition (area %) | C14:0 | 1.55 | 1.59 | 1.64 | 1.68 | 1.71 | 1.74 | 1.64 | 1.81 | 2.65 |
| | C14:1 | 0.27 | 0.27 | 0.25 | 0.25 | 0.16 | 0.15 | 0.14 | 0.21 | 0.26 |
| | C16:0 | 4.88 | 4.53 | 5.94 | 7.40 | 10.29 | 10.20 | 9.67 | 9.80 | 17.38 |
| | C16:1 | 3.13 | 3.17 | 2.99 | 2.89 | 2.91 | 3.01 | 2.84 | 2.62 | 4.70 |
| | C16:2 | 1.44 | 1.38 | 1.31 | 1.17 | 1.08 | 1.13 | 0.98 | 1.35 | 1.22 |
| | C18:0 | 1.99 | 1.62 | 1.78 | 2.31 | 2.85 | 2.88 | 2.71 | 3.95 | 4.96 |
| | C18:1 n-9 | 11.33 | 11.26 | 10.60 | 10.05 | 9.42 | 9.69 | 9.37 | 8.59 | 16.34 |
| | C18:1 n-7 | 1.74 | 1.80 | 1.68 | 1.56 | 1.43 | 1.47 | 1.42 | 1.51 | 2.41 |
| | C18:2 n-6 | 0.82 | 0.83 | 0.71 | 0.67 | 0.65 | 0.67 | 0.67 | 0.59 | 1.16 |
| | C18:3 n-3 | 0.28 | 0.00 | 0.26 | 0.26 | 0.25 | 0.26 | 0.25 | 0.37 | 0.31 |
| | C18:3 n-6 | 0.40 | 0.41 | 0.35 | 0.36 | 0.36 | 0.37 | 0.34 | 0.33 | 0.53 |
| | C18:4 n-3 | 1.37 | 1.36 | 1.33 | 1.21 | 1.12 | 1.20 | 1.00 | 1.35 | 0.82 |
| | C20:0 | 0.27 | 0.25 | 0.26 | 0.27 | 0.29 | 0.29 | 0.33 | 0.36 | 0.29 |
| | C20:1 | 1.81 | 1.75 | 0.53 | 0.50 | 2.03 | 2.09 | 2.29 | 3.02 | 2.64 |
| | C20:3 n-3 | 0.21 | 0.21 | 0.20 | 0.18 | 0.48 | 0.43 | 0.00 | 0.26 | 0.24 |
| | C20:4 n-6 | 2.78 | 2.80 | 2.83 | 2.72 | 2.70 | 2.74 | 2.70 | 2.78 | 1.82 |
| | C20:4 n-3 | 0.61 | 0.59 | 0.52 | 0.47 | 0.41 | 0.43 | 0.43 | 0.70 | 0.53 |
| | EPA | 7.61 | 7.32 | 6.98 | 6.24 | 5.79 | 5.93 | 6.06 | 9.38 | 6.55 |
| | C22:5 n-3 | 2.33 | 2.34 | 2.55 | 2.48 | 2.63 | 2.61 | 2.44 | 2.29 | 1.60 |
| | DHA | 44.32 | 45.52 | 47.47 | 47.84 | 47.86 | 47.06 | 48.76 | 41.56 | 23.61 |
| EPA + DHA (area %) | | 51.93 | 52.84 | 54.45 | 54.08 | 53.65 | 52.98 | 54.82 | 50.95 | 30.17 |
| Saturated fatty acid (area %) (C14:0 + C16:0 + C18:0) | | 8.42 | 7.74 | 9.36 | 11.40 | 14.85 | 14.81 | 14.02 | 15.56 | 24.99 |
| Acid value (AV) | | 113.9 | 129.7 | 124.5 | 125.2 | 124.2 | 125.1 | 112.4 | 91.6 | |

TABLE 7

| | | Reaction temperature | | | | | | | Refined fish oil 2 |
|---|---|---|---|---|---|---|---|---|---|
| | | 10 | 15 | 20 | 25 | 30 | 35 | 40 | |
| Fatty acid composition (area %) | C14:0 | 1.88 | 1.68 | 1.78 | 1.75 | 1.73 | 1.57 | 1.56 | 2.56 |
| | C16:0 | 7.15 | 4.57 | 5.13 | 6.73 | 8.54 | 11.84 | 11.88 | 20.52 |
| | C16:1 | 3.99 | 3.73 | 3.69 | 3.35 | 3.27 | 2.83 | 2.81 | 4.77 |
| | C18:0 | 3.07 | 2.19 | 2.22 | 2.82 | 3.36 | 3.49 | 3.49 | 5.76 |
| | C18:1 | 15.20 | 13.94 | 13.65 | 12.43 | 11.78 | 9.82 | 9.85 | 17.16 |
| | C18:2 n-6 | 0.95 | 0.89 | 0.87 | 0.76 | 0.73 | 0.64 | 0.61 | 1.09 |
| | C18:4 n-3 | 0.91 | 0.96 | 0.92 | 0.84 | 0.83 | 0.75 | 0.76 | 0.60 |
| | C20:4 | 3.04 | 3.16 | 3.10 | 3.00 | 2.95 | 2.82 | 2.77 | 2.19 |
| | EPA | 5.75 | 5.68 | 5.44 | 5.14 | 4.77 | 4.31 | 4.27 | 5.11 |
| | C22:5 n-3 | 1.94 | 2.07 | 2.08 | 2.03 | 2.02 | 1.97 | 1.97 | 1.35 |
| | DHA | 41.38 | 46.34 | 46.52 | 46.63 | 45.78 | 46.23 | 46.12 | 24.22 |
| EPA + DHA (area %) | | 47.13 | 52.02 | 51.96 | 51.77 | 50.55 | 50.54 | 50.39 | 29.33 |
| Saturated fatty acid (area %) (C14:0 + C16:0 + C18:0) | | 12.10 | 8.44 | 9.13 | 11.30 | 13.63 | 16.90 | 16.93 | 28.84 |
| Acid value (AV) | | 100.9 | 111.8 | 117.1 | 116.2 | 115.2 | 111.8 | 115.1 | |

Figure 5:
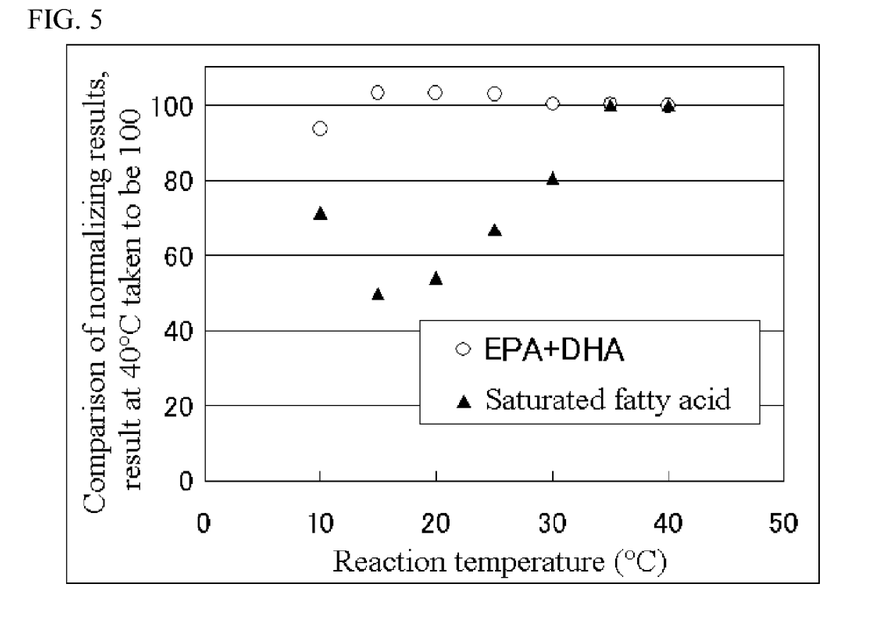
FIG. 5 is a graph showing proportions of saturated fatty acid and EPA+DHA contained in the glyceride fraction treated with lipase at each reaction temperature in Production Example 2, normalized such that results for the reaction at 40° C. are 100.

The aforementioned results are shown in FIG. 5, which shows the EPA and DHA content and the saturated fatty acid content of the glyceride fraction under each temperature condition, when the result for the 40° C. reaction oil is normalized to 100. From this chart, under 10 to 25° C. temperature conditions, it is understood that there was a great decrease in the saturated fatty acid content, while the EPA and DHA contents remained high.

Production Example 3

4 mL of water and 13.3 mg (600 units/mL oil) or 6.7 mg (300 units/mL oil) of Lipase OF were added to 8 mL of refined fish oil 1, and the mixture was stirred using a blade-equipped agitator. The reaction temperature was set to 20° C. After 2, 5, 8, 14, and 20 hours, a sample was obtained (about 1 to 2 g), and lipase of the sample was deactivated by heating for 10 minutes at 80° C. Thereafter, the mixture was separated into an oil layer and aqueous layer using a centrifugal separator (40° C., 1,800 g, 10 min) to obtain the reaction oil.

Figure 6:
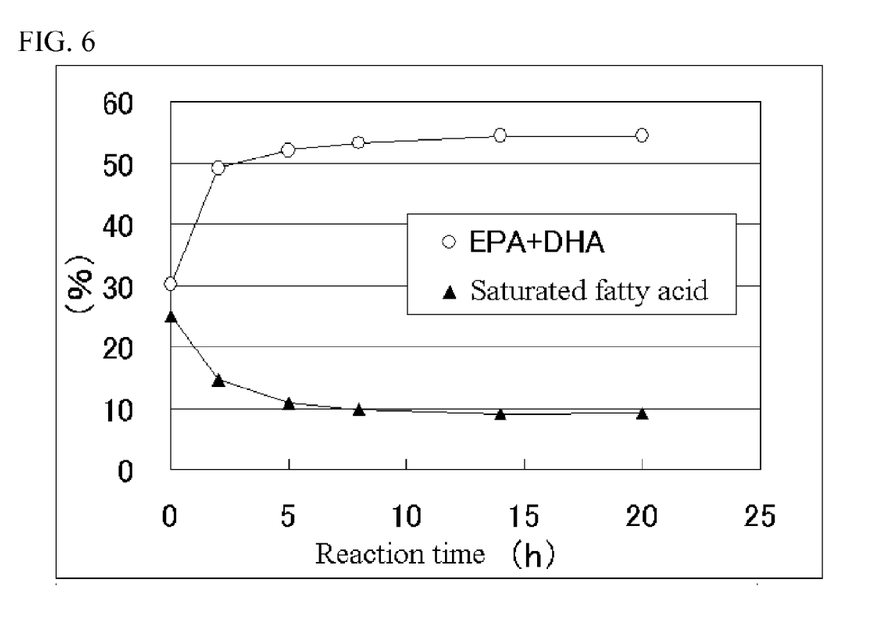
FIG. 6 is a graph showing change over time of saturated fatty acid, EPA, and DHA amounts during the lipase reaction of Production Example 3 (20° C., 600 units/mL oil).
Figure 7:
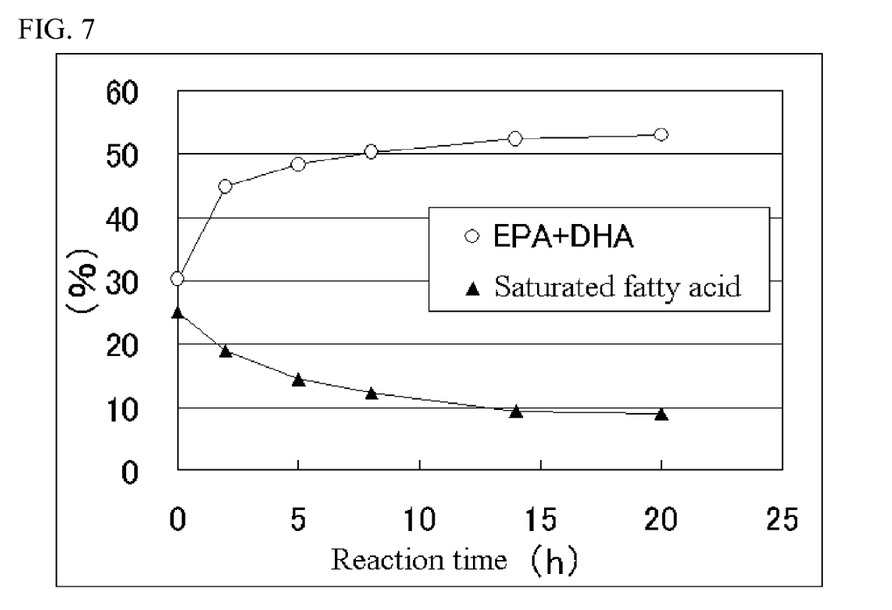
FIG. 7 is a graph showing change over time of saturated fatty acid, EPA, and DHA amounts during the lipase reaction of Production Example 3 (20° C., 300 units/mL oil).

The saturated fatty acid content (area %) and the EPA and DHA content (area %) at each time interval are shown in FIGS. 6 and 7. The saturated fatty acid content decreased greatly with reaction time, and the EPA and DHA content increased with reaction time.

Comparative Example 2

Except for setting the reaction temperature to 40° C., the reaction was performed by the same procedure and under the same conditions as Production Example 3 using 600 units/mL of the lipase.

Figure 8:
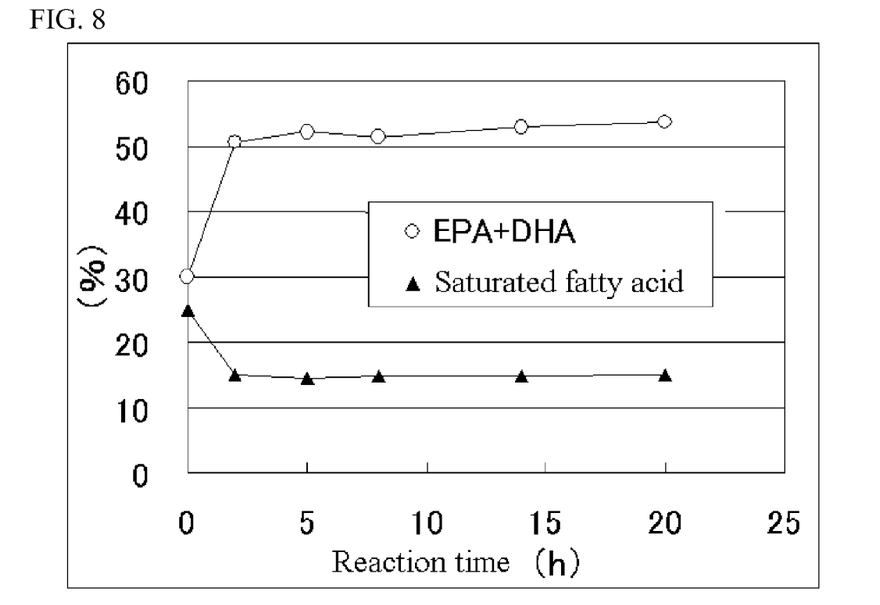
FIG. 8 is a graph showing change over time of saturated fatty acid, EPA, and DHA amounts during the lipase reaction of Comparative Example 2 (40° C., 600 units/mL oil).

The saturated fatty acid content (area %) and the EPA and DHA content (area %) at each time interval are shown in FIG. 8. Although the saturated fatty acid content decreased down to 15.0% at 2 hours of reaction time, further decrease was not found even when the reaction time was further prolonged, and there was a shift to a high saturated fatty acid content of about 15%.

Production Example 4 and Comparative Example 3

To 3 mL of refined fish oil 3 (deacidified tuna oil, Nippon Suisan Kaisha, Ltd.) were added 1.5 mL of water and 5 mg of Lipase OF (600 units/mL oil). A magnetic stirrer was used to stir the mixture for 14 hours in a constant-temperature bath at 20° C. After the 14 hours of stirring, about 2 mL of the reaction oil was sampled, and the lipase was deactivated by heating for 10 minutes at 80° C. Thereafter, the mixture was separated into an oil layer and aqueous layer using a centrifugal separator (40° C., 1,800 g, 10 min) to obtain the reaction oil.

As a Comparative Example 3, the reaction was performed under the same conditions as those mentioned above for Production Example 4, except for change of temperature to 40° C. Except for temperature, all conditions and procedures were the same.

Figure 9:
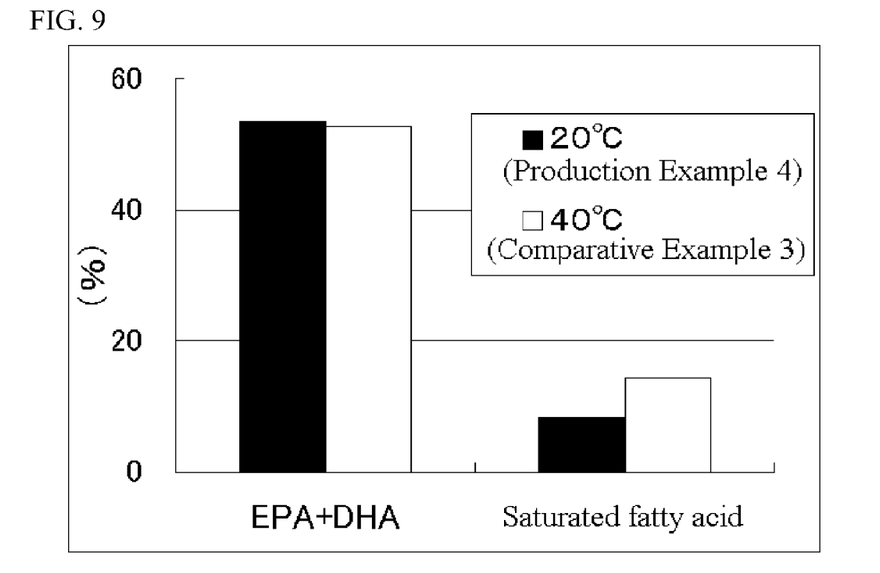
FIG. 9 is a graph showing a comparison of saturated fatty acid, EPA, and DHA amounts in the lipase reaction of Production Example 4 (20° C.) and Comparative Example 3 (40° C.).

The saturated fatty acid content (area %) and the EPA and DHA content (area %) of Production Example 4 and Comparative Example 3 are shown in FIG. 9. From this chart, it is understood that the saturated fatty acid content greatly decreased and the EPA and DHA content somewhat increased under the 20° C. temperature condition in comparison to 40° C. temperature condition.

Production Example 5

6,000 L of refined fish oil 4 (deacidified tuna oil, Nippon Suisan Kaisha, Ltd.), 3,000 L of water, and 5 kg of Lipase OF (300 unit/mL oil) were loaded into a reaction vessel, and reaction was carried out by stirring for 21 hours while maintaining temperature at from 20 to 25° C. After the 21 hours of stirring, about 50 g of the reaction oil was sampled, the lipase was deactivated by heating for 10 min at 80° C., and a supernatant reaction oil was obtained.

Figure 10:
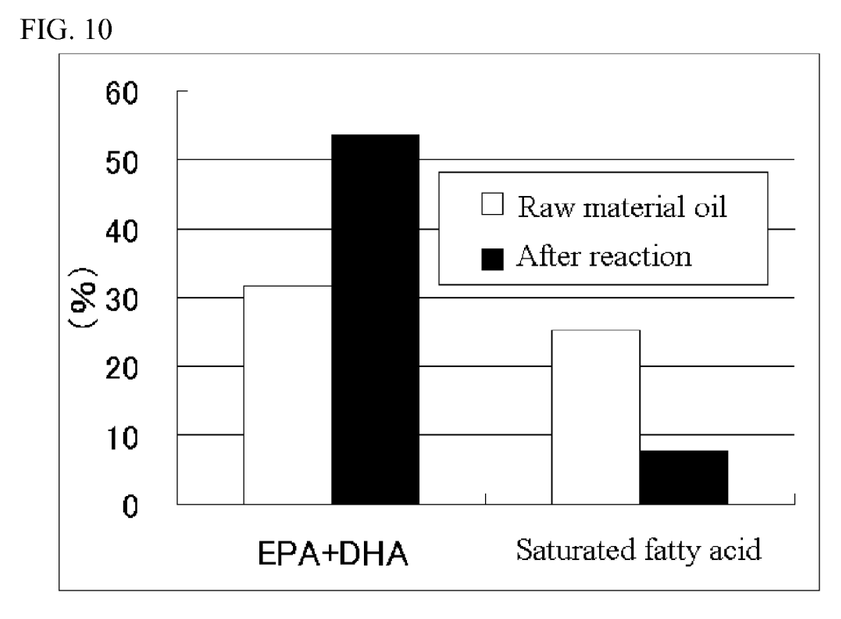
FIG. 10 is a graph showing results of the large-scale reaction of Production Example 5.

Saturated fatty acid content (area %) and EPA and DHA content (area %) of the refined fish oil, and saturated fatty acid content (area %) and EPA and DHA content (area %) of the glyceride fraction of the reaction oil are shown in FIG. 10. Even when the reaction was performed at a large scale, it was confirmed that EPA and DHA concentration increased and that the saturated fatty acid content decreased greatly to not more than 10%.

Production Example 6

Lipid composition (area %) was measured in the glyceride fraction of the reaction oils produced under the 10, 20, 40, and 50° C. reaction conditions of Production Example 1. As shown in Table 8, it was possible to obtain a triglyceride proportion having a triglyceride proportion of at least 80 area % when the reaction was performed at 10 and 20° C. On the other hand, the triglyceride proportion was about 72.8 area % and 59.9 area % when the reaction was performed at 40 and 50° C., respectively. By performing the lipase reaction at low temperature, in addition to being able to lower the saturated fatty acid content, it was shown possible to increase the triglyceride proportion.

TABLE 8

| Reaction temperature (° C.) | | 10 | 20 | 40 | 50 |
|---|---|---|---|---|---|
| Lipid Composition (%) | Triglyceride | 82.6 | 82.4 | 72.8 | 59.9 |
| | Diglyceride | 15.5 | 14.6 | 18.7 | 30.4 |
| | Monoglyceride | 1.9 | 3.0 | 8.4 | 9.8 |

INDUSTRIAL APPLICABILITY

One object of intake of fatty acids having physiological activity (i.e. EPA, DHA, or the like) is to prevent diseases of the heart and vascular system such as hypercholesterolemia. Although cholesterols are important as a source of calories, the modern diet often results in excessive intake of cholesterols, particularly during middle age, and aggressive intake of cholesterols is undesirable. Particularly, for people who need to take preventive measures for heart and vascular system diseases, when highly unsaturated fatty acid is ingested, the amount of co-ingested cholesterol is preferably as low as possible. The oil produced by the present invention concentrates highly unsaturated fatty acid and further reduces the amount of cholesterol. The present invention is thus suitable for use as a health food or supplement for supplying n-3 type highly unsaturated fatty acids.

The invention claimed is:

1. A method for lowering content of a sterol in a highly unsaturated fatty acid-concentrated oil in a method to concentrate a highly unsaturated fatty acid by using a lipase reaction, which comprises the steps of: removing the free form of the sterol from a raw material oil that includes a highly unsaturated fatty acid-containing glyceride prior to performing the lipase reaction; and thereafter concentrating the highly unsaturated fatty acid in the glyceride by using a lipase that is less reactive for the highly unsaturated fatty acid.

2. The method according to claim 1, wherein the sterol is cholesterol.

3. A method for producing a highly unsaturated fatty acid-containing glyceride by using the method described in claim 2, wherein the content of the cholesterol in the glyceride is 0.3 weight % or less, and the content of the highly unsaturated fatty acid in the fatty acids of the glyceride is 40 area % or more.

4. The method for producing a highly unsaturated fatty acid-containing glyceride according to claim 3, wherein the lipase reaction is performed at a temperature of 25° C. or below, the content of the cholesterol in the glyceride is 0.3 weight % or less, the content of the highly unsaturated fatty acid in the glyceride is 40 area % or more, and the proportion of saturated fatty acids in the fatty acids in the glyceride is 12 area % or less.

5. The method according to claim 3, wherein the lipase is derived from a microbe selected from the group consisting of Candida cylindracea, Alcaligenes sp., Burkholderia cepacia, Pseudomonas fluorescens, Thermomyces lanuginosa, Rhizomucor miehei, and Pseudomonas sp.

6. The method according to claim 3, wherein the cholesterol is removed by a distillation process.

7. The method according to claim 6, wherein the distillation process is performed at a temperature of from 200 to 270° C.

8. The method according to claim 6, wherein the distillation process is performed at a temperature of from 220 to 260° C.

9. The method according to claim 6, wherein the distillation process is performed at a pressure of 5 Pa or less.

10. The method according to claim 6, wherein the distillation process is performed at a pressure of 2 Pa or less.

11. The method according to claim 6, wherein a flux rate of the distillation process is from 20 to 200 (kg/h)/m$^2$.

12. The method according to claim 6, wherein a flux rate of the distillation process is from 20 to 150 (kg/h)/m$^2$.

13. The method according to claim 6, wherein the distillation process is a distillation method selected from the group consisting of thin film distillation, molecular distillation, and short path distillation or a combination thereof.

14. The method according to claim 3, wherein the highly unsaturated fatty acid is selected from the group consisting of docosahexaenoic acid (DHA), eicosapentaenoic acid (EPA), arachidonic acid (ARA), and dihomo-γ-linolenic acid (DGLA).

15. The method according to claim 14, wherein the raw material oil is selected from the group consisting of fish oils and microbial oils.

16. A highly unsaturated fatty acid-containing glyceride, wherein the content of sterol is 0.3 weight % or less, and the content of highly unsaturated fatty acid in the fatty acids of the glyceride is 40 area % or more, and the proportion of the saturated fatty acids in the fatty acids is 12 area % or less.

17. The glyceride according to claim 16, wherein the sterol is cholesterol.

18. The glyceride according to claim 16, wherein proportion of triglyceride in the glyceride is not less than 80 area %.

19. The glyceride according to claim 16, wherein the highly unsaturated fatty acid is selected from the group consisting of docosahexaenoic acid (DHA), eicosapentaenoic acid (EPA), arachidonic acid (ARA), and dihomo-γ-linolenic acid (DGLA).

* * * * *